US012691110B2

(12) United States Patent
Kim et al.

(10) Patent No.: US 12,691,110 B2
(45) Date of Patent: Jul. 28, 2026

(54) TOPOTECAN FOR PROLIFERATIVE VITREORETINOPATHY

(71) Applicant: Massachusetts Eye and Ear Infirmary, Boston, MA (US)

(72) Inventors: Leo A. Kim, Brookline, MA (US); Joseph F. Arboleda-Velasquez, Newton, MA (US); Dean Eliott, Boston, MA (US); Elizabeth Jeffries Rossin, Charlestown, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 476 days.

(21) Appl. No.: 18/193,270

(22) Filed: Mar. 30, 2023

(65) Prior Publication Data

US 2023/0355611 A1 Nov. 9, 2023

Related U.S. Application Data

(60) Provisional application No. 63/325,459, filed on Mar. 30, 2022.

(51) Int. Cl.

| | |
|---|---|
| ***A61K 31/475*** | (2006.01) |
| ***A61K 9/00*** | (2006.01) |
| ***A61K 45/06*** | (2006.01) |
| ***A61P 27/02*** | (2006.01) |

(52) U.S. Cl.

CPC .......... *A61K 31/475* (2013.01); *A61K 9/0019* (2013.01); *A61K 9/0048* (2013.01); *A61K 45/06* (2013.01); *A61P 27/02* (2018.01)

(58) Field of Classification Search

CPC .. A61K 31/475; A61K 9/0019; A61K 9/0048; A61K 45/06; A61P 27/02

See application file for complete search history.

(56) References Cited

U.S. PATENT DOCUMENTS

| | | | | |
|---|---|---|---|---|
| 3,405,122 | A | 10/1968 | Berger et al. | |
| 5,036,101 | A | 7/1991 | Hsu et al. | |
| 5,041,438 | A | 8/1991 | Hsu | |
| 5,141,735 | A | 8/1992 | Bellemin et al. | |
| 5,164,376 | A | 11/1992 | Hsu et al. | |
| 5,641,773 | A | 6/1997 | Pardee et al. | |
| 9,173,775 | B2 | 11/2015 | Haffner et al. | |
| 9,668,915 | B2 | 6/2017 | Haffner et al. | |
| 10,285,853 | B2 | 5/2019 | Rangel-Friedman et al. | |
| 2006/0035955 | A1 | 2/2006 | Zeldis | |
| 2014/0004082 | A1 | 1/2014 | Liu et al. | |
| 2017/0128424 | A1* | 5/2017 | Rothstein | A61K 9/5031 |
| 2018/0369017 | A1 | 12/2018 | Schieber et al. | |
| 2020/0377888 | A1 | 12/2020 | Kim et al. | |
| 2021/0030590 | A1 | 2/2021 | Blanda et al. | |

FOREIGN PATENT DOCUMENTS

WO WO-2022229932 A1 * 11/2022 ........... A61K 31/185

OTHER PUBLICATIONS

Miwa et al. (Pharmacological HIF inhibition prevents retinal neovascularization with improved visual function in a murine oxygen-induced retinopathy mode), Neurochemistry International 128 (2019) 21-31.*

Amarnani et al., "Abstract: Identification of Drug Candidates using a Patient-Derived Model of Proliferative Vitreoretinopathy," Abstract, Presented at Proceedings of the 2021 ARVO Annual Meeting, Virtual, Jun. 2021; 62(8):3643, 2 pages.

Amarnani et al., "Poster: Identification of Drug Candidates using a Patient-Derived Model of Proliferative Vitreoretinopathy," Poster, Presented at Proceedings of the 2021 ARVO Annual Meeting, Virtual, Jun. 2021, 1 page.

Asato et al., "Comparison of gene expression profile of epiretinal membranes obtained from eyes with proliferative vitreoretinopathy to that of secondary epiretinal membranes," PLoS One, 2013, 8(1):e54191, 8 pages.

Cunningham et al., "Identification of benzodiazepine Ro5-3335 as an inhibitor of CBF leukemia through quantitative high throughput screen against RUNX1-CBFβ interaction," Proc Natl Acad Sci USA, Sep. 2012, 109(36):14592-14597.

Haghjou et al., "Sustained release intraocular drug delivery devices for treatment of uveitis," J Ophthalmic Vis Res., Oct. 2011, 6(4):317-329.

Haubrich et al., "A randomized trial of the activity and safety of Ro 24-7429 (Tat antagonist) versus nucleoside for human immunodeficiency virus infection. The AIDS Clinical Trials Group 213 Team," J Infect Dis, Nov. 1995, 172(5):1246-52.

Hiscott et al., "Pathobiology of epiretinal and subretinal membranes: possible roles for the matricellular proteins thrombospondin 1 and osteonectin (SPARC)," Eye, Jul. 2002, 16(4):393-403.

Hiscott et al., "Retinal pigment epithelial cells in epiretinal membranes: an immunohistochemical study," Br J Ophthalmol., Oct. 1984, 68(10):708-15.

Kim et al., "Controlled drug release from an ocular implant: an evaluation using dynamic three-dimensional magnetic resonance imaging," Invest. Ophthalmol. Vis. Sci., Aug. 2004, 45(8):2722-2731.

Lean et al., "Classification of proliferative vitreoretinopathy used in the silicone study. The Silicone study group," Ophthalmology, Jun. 1989, 96(6):765-771.

Lee et al., "Biodegradable implants for sustained drug release in the eye," Pharm Res., Oct. 2010, 27(10):2043-53.

Machemer et al., "An updated classification of retinal detachment with proliferative vitreoretinopathy," Am J Ophthalmol, Aug. 1991, 112(2):159-65.

(Continued)

*Primary Examiner* — Zohreh A Fay

(74) *Attorney, Agent, or Firm* — Fish & Richardson P.C.

(57) ABSTRACT

The use of topotecan, e.g., repeated dosing or sustained-release formulations of topotecan, for treating or reducing risk of proliferative vitreoretinopathy (PVR) or epiretinal membranes (ERM), e.g., after surgical vitrectomy to treat retinal detachment, is described herein.

20 Claims, 7 Drawing Sheets

(56) References Cited

OTHER PUBLICATIONS

Palakurthi et al., "Investigation of kinetics of methotrexate for therapeutic treatment of intraocular lymphoma," Current Eye Research, Oct. 2010, 35(12):1105-1115.
Patankar et al., "Topophore C: a liposomal nanoparticle formulation of topotecan for treatment of ovarian cancer," Invest New Drugs, Feb. 2013, 31(1):46-58.
Souza et al., "Development of topotecan loaded lipid nanoparticles for chemical stabilization and prolonged release," Eur J Pharm Biopharm, Sep. 2011, 79(1):189-96.
Taich et al., "Sustained-release hydrogels of topotecan for retinoblastoma," Colloids Surf B Biointerfaces, Oct. 2016, 146:624-31.
The Retina Society Terminology Committee, "The classification of retinal detachment with proliferative vitreoretinopathy," Ophthalmology, Feb. 1983, 90(2):121-5.
Velez and Whitcup, "New developments in sustained release drug delivery for the treatment of intraocular disease," Br J Ophthalmol, 1999, 83:1225-1229.
Falavarjani et al., "Intrasilicone oil injection of bevacizumab at the end of retinal reattachment surgery for severe proliferative vitreoretinopathy," Eye, Feb. 2014, 28(5):576-580.
Grierson et al., "Non-vascular vitreoretinopathy: the cells and the cellular basis of contraction," Eye, Nov. 1996, 10(6):671-684.
Jusufbegovic et al., "Risk factors and prevention of proliferative vitreoretinopathy," Expert Review of Ophthalmology, Sep. 2015, 10(5):431-440.

* cited by examiner

TOPOTECAN FOR PROLIFERATIVE VITREORETINOPATHY

CLAIM OF PRIORITY

This application claims the benefit of U.S. Patent Application Ser. No. 63/325,459, filed on Mar. 30, 2022. The entire contents of the foregoing are hereby incorporated by reference.

STATEMENT REGARDING FEDERAL FUNDING

This invention was made with government support under Grant No. W81XWH-17-2-0006 awarded by the Department of Defense. The government has certain rights in the invention.

TECHNICAL FIELD

This invention relates to the use of topotecan, e.g., multiple intravitreal injections of topotecan, for treating or reducing the risk of proliferative vitreoretinopathy (PVR) and treating retinal detachment.

BACKGROUND

Retinal detachment (RD) is an important cause of sudden visual loss in the United States, with approximately 40,000 cases occurring annually. Permanent visual loss will result if treatment is delayed.

A retinal detachment is defined as the separation of the neurosensory retina from the retinal pigment epithelium (RPE). In the nonpathologic state, the retinal pigment epithelium is a continuous epithelial monolayer occluded by tight junctions, which maintain a strict separation of the underlying choroidal capillary beds from the photoreceptors of the sensory retina, thus forming the outer blood-retina barrier. Its functions include the nourishment of photoreceptors, elimination of waste products, and reabsorption of subretinal fluid.

The definitive treatment of retinal detachment is surgical repair. Multiple operative techniques are available to the treating retinologist, but the principles underlying treatment of retinal detachment remain the same: removal of fluid from the subretinal space, relief of any existing traction, and treatment and prophylaxis against the underlying cause for the ingression of fluid, whether it be due to a retinal break or an exudative process.

Proliferative vitreoretinopathy (PVR) is a common complication of post-traumatic eye surgery, in which cells grow uncontrollably beneath or on top of the retina triggering pre/sub-retinal membrane formation, tractional retinal detachment, and permanent vision loss. PVR occurs in 40-60% of patients with open globe injury.

SUMMARY

The present invention is based, at least in part, on the development of methods to treat and to reduce the risk of developing PVR using topotecan.

Described herein are methods of treating or reducing the risk of proliferative vitreoretinopathy (PVR) in a subject. The methods comprise administering multiple intravitreal injections of topotecan over a period of at least one, two, three, four, or more months, given no more frequently than weekly.

In some embodiments, the methods comprise administering five or more intravitreal injections of topotecan. In some embodiments, the methods comprise administering seven intravitreal injections of topotecan. In some embodiments, each injection provides a dose of about 5 mcg, about 6 mcg, about 7 mcg, about 8 mcg, about 9 mcg, or about 10 mcg topotecan, preferably administered in a volume of 0.1 ml (e.g., in a physiologically acceptable carrier, such as saline). In some embodiments, each injection provides a dose of about 8 mcg topotecan, preferably administered in a volume of 0.1 ml.

In some embodiments, the subject is undergoing an ocular surgical procedure that increases the subject's risk of developing PVR. In some embodiments, the ocular surgical procedure is a pars plana vitrectomy (PPV), Retinal Detachment (RD) surgery; ERM surgery; scleral buckle surgery; or a procedure in the other eye. In some embodiments, the subject requires a PPV to treat a rhegmatagenous retinal detachment (RRD) secondary to trauma; preexisting proliferative vitreoretinopathy; or for other indications associated with high risk condition for PVR development.

In some embodiments, the indication associated with high risk condition for PVR development is a giant retinal tear, a retinal break larger than 3 disc areas, a long-standing retinal detachment, or a detachment associated with hemorrhage.

In some embodiments, the topotecan is administered preoperatively, intraoperatively during surgery, and/or postoperatively.

In some embodiments, a first injection is given preoperatively within one week from surgery; a second injection is given intraoperatively during surgery; and five or more injections are given postoperatively, preferably at 2 weeks, 4 weeks, 8 weeks, 12 weeks and 16 weeks postoperatively.

In some embodiments, the methods comprise administering additional injections after the seventh injection.

In some embodiments, the topotecan is administered in combination with one or more additional therapeutic agents. In some embodiments, the one or more additional therapeutic agents is melphalan, daunorubicin, lenalidomide, daclatsvir, stavudine, resveratrol, marbofloxacin, bendamustine HCl, semagacestat, methotrexate, or a Runx1 inhibitor, or an analogue thereof, e.g., as described herein.

In some embodiments, the one or more additional therapeutic agents is administered simultaneously with the topotecan.

In some embodiments, the topotecan is administered posterior to the limbus.

Also provided herein are methods for treating or reducing the risk of PVR in a subject. The methods comprise intravitreally administering a sustained release formulation of topotecan over at least a four-month period. In some embodiments, the sustained release formulation is or comprises a lipid-encapsulated formulation; multivesicular liposome (MVL) formulations of topotecan; nano- or microparticles; polyion complex (PIC) micelles; or bioadhesive polymers. In some embodiments, the bioadhesive polymers comprise one or more of hydroxypropyl methylcellulose (HPMC), carboxymethylcellulose (CMC), polyacrylic acid (PAA), or hyaluronic acid (HA).

Additionally, provided herein are methods of treating or reducing the risk of PVR in a subject. The methods comprise implanting into the eye of the subject a device that provides sustained release of topotecan, and optionally one or more additional therapeutic agents, over at least a four-month period, preferably wherein the device is implanted within a week before the subject undergoes an ocular surgical procedure that increases the subject's risk of developing PVR.

Melphalan or analogs thereof can be used as an alternative to topotecan in any of the methods or compositions described herein, including in combination with the other therapeutic agents such as RUNX1 inhibitors or daunorubicin or analogs thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A shows the CyQuant cell proliferation assay data for melphalan at concentrations of 30 μM and 60 μM. FIG. 1B shows the CyQuant cell proliferation assay data for topotecan HCl at concentrations of 40 nM and 80 nM.

FIGS. 2A-2B show the CyQuant cell proliferation assay data on proliferation of C-PVR cells measured 48 and 72 hours post treatment respectively with topotecan HCl (80 nM) alone or in combination with the validated hits, melphalan (30 μM), Daunorubicin (30 nM), Lenalidomide (80 nM), Daclatsvir (5 μM), Stavudine (5 μM), Resveratrol (5 μM), Marbofloxacin (5 μM), Bendamustine HCl (5M), Semagacestat (5 μM), and Methotrexate (400 μM) compared to vehicle treated controls. *P<0.05, P<0.01, *P<0.001, ****P<0.0001.

FIGS. 3A-3B show the CyQuant cell proliferation assay data on proliferation of C-PVR cells measured 48 and 72 hours post treatment respectively with melphalan (30 μM) alone or in combination with the validated hits, topotecan HCl (80 nM), Daunorubicin (30 nM), Lenalidomide (80 nM), Daclatsvir (5 μM), Stavudine (5 μM), Resveratrol (5 μM), Marbofloxacin (5 μM), Bendamustine HCl (5 μM), Semagacestat (5 μM), and Methotrexate (400 μM) compared to vehicle treated controls. *P<0.05, P<0.01, *P<0.001, ****P<0.0001.

FIG. 5A shows the percent of cells (y-axis) across all 7 samples that expressed the PVR gene of interest (x-axis). Expression was defined as any cell containing at least 1 transcript of the target gene. FIG. 5B shows the mean log-normalized expression of PVR genes of interest across cells expressing at least 1 transcript.

DETAILED DESCRIPTION

Figure 1A:
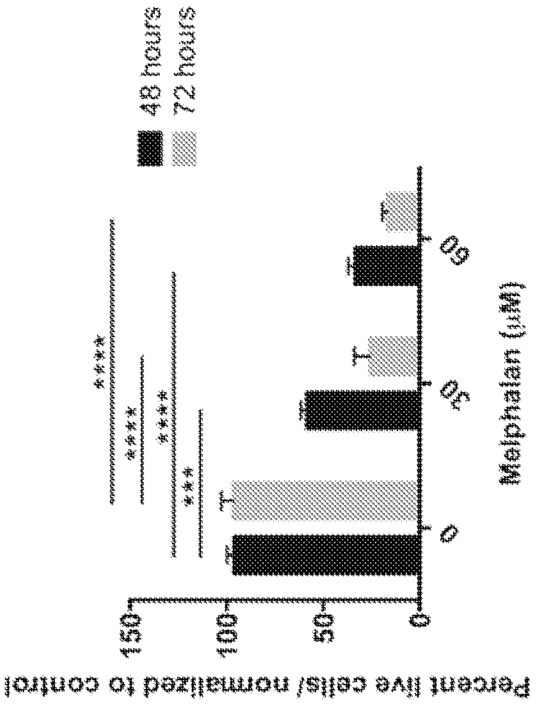
FIGS. 1A-1B show the effect of candidate drugs on proliferation of human patient derived primary cultures (C-PVR).

Migration and proliferation of retinal cells, the formation of contractile membranes, and subsequent tractional detachment of the retina are hallmarks of PVR. Currently, there are no specific therapeutic agents used for the prevention or treatment of PVR. Different pharmacological agents have been tested as monotherapies for the treatment of PVR with different activities including anti-inflammatory, anti-proliferative, anti-neoplastic, and anti-growth-factor agents; albeit without success.

Accordingly, there exists a need in the art for treating and/or reducing the risk of PVR and treating retinal detachment.

The present disclosure relates to methods of treating or reducing the risk of PVR using topotecan alone or in combination with one or more additional therapeutic agents (e.g., melphalan, daunorubicin, lenalidomide, daclatsvir, stavudine, resveratrol, marbofloxacin, bendamustine HCl, semagacestat, methotrexate, or Runx1 inhibitors, or analogs thereof) for a potential synergistic effect.

Pathobiology of Proliferative Vitreoretinopathy (PVR) and Epiretinal Membranes (ERM)

Proliferative vitreoretinopathy (PVR) is a common occurrence after retinal detachment surgery. PVR is a “scarring” condition that forms inside the eye after surgery, significant trauma, or even spontaneously. Its pathogenesis is the disruption of the retinal pigment epithelium layer, which is associated with inflammation, migration, and proliferation of cells to the (neural) retinal surface. Over the next 4-12 weeks, membranes on the surface of the retina proliferate, contract, and apply traction on the retina, which results in redetachment of the retina from the RPE. Once PVR is present and the retina detaches for a second time, it is unlikely that vision will be restored.

Proliferative vitreoretinopathy (PVR) is the most common cause for failure of retinal detachment surgery, a complication which occurs in 5-10% of all retinal detachment surgeries. PVR can also occur spontaneously in the absence of surgery. PVR is most likely to develop following repeated surgical instrumentation of the eye, following significant physiologic insult to the eye such as in trauma, as well as in retinal detachments complicated by multiple tears, giant tears, vitreous hemorrhage, or in eyes with uveitis.

A milder form of PVR, called macular pucker or epiretinal membrane (ERM), complicates the post-operative course of 20-30% of RD surgeries and half of these are so visually distorting that patients will require surgery. In addition, autopsy studies show that close to 75-80% of patients with RD surgery have histological evidence of proliferative membranes. This may explain why many patients do not achieve perfect vision postoperatively after RD surgery, yet do not have any clinically obvious ERMs. In addition, ERMs can also develop spontaneously.

Epiretinal membranes (ERM) are caused by an abnormal proliferation of cells, e.g., retinal pigment epithelial (RPE) cells, glial cells, fibroblasts, and macrophages, on the surface of the retina, typically in response to ocular disease; the membranes tend to contract and cause puckering and thus distortion of the macula. See, e.g., Hiscott et al., Br J Ophthalmol. 68(10):708-15 (1984); Hiscott et al., Eye 16, 393-403 (2002); and Asato et al., PLoS One. 8(1): e54191 (2013).

Like ERM, PVR is an abnormal wound healing response of the vitreous and retina, a clinical syndrome where cells with proliferative capacity, driven by inflammatory mediators, multiply on the retinal surface, contract, and eventually cause recurrent retinal detachment (RD). The pathogenesis of PVR begins with the introduction of RPE cells into the vitreous cavity. These cells may be introduced at the time of the retinal tear itself or may be introduced iatrogenically such as through the use of cryotherapy or retinectomy. Studies from monkey eyes with PVR have also postulated that the introduction of Müller cells, as well as potentially fibrocytes, occur as well. Concomitant with the introduction of RPE cells is the introduction or upregulation of growth factors, including vascular endothelial growth factor (VEGF), platelet-derived growth factor (PDGF), fibronectin, transforming growth factor-beta (TGF-β), and other mediators. This process begins an autocrine loop where glial, RPE, and other cellular constituents proliferate and transdifferentiate into contractile myofibrocytes. On pathology, macrophages as well as fibroblasts are commonly identified in specimens of PVR.

Topotecan

Topotecan is a semisynthetic derivative of camptothecin, a cytotoxic, quinoline-based alkaloid extracted from the Asian tree *Camptotheca acuminata*. Topotecan inhibits topoisomerase I activity by stabilizing the topoisomerase I-DNA covalent complexes during S phase of cell cycle, thereby inhibiting re-ligation of topoisomerase I-mediated single-strand DNA breaks and producing potentially lethal double-strand DNA breaks when encountered by the DNA replication machinery.

The chemical structure of topotecan is shown in Formula I:

Formula I

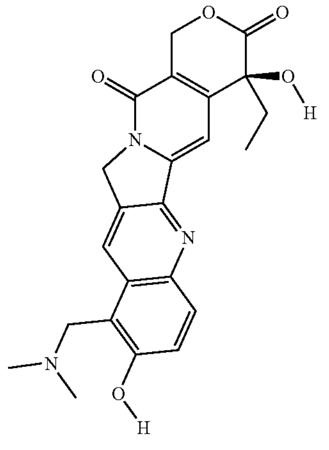

In some embodiments, the topotecan is administered in the form of topotecan hydrochloride (topotecan HCl).

In some embodiments, the topotecan (and/or one or more additional therapeutic agents, e.g., melphalan, daunorubicin, lenalidomide, daclatsvir, stavudine, resveratrol, marbofloxacin, bendamustine hcl, semagacestat, methotrexate, or RUNX1 inhibitors, or analogs thereof, e.g., as described herein) is formulated for repeated injection, e.g., in a physiologically acceptable carrier such as saline, e.g., phosphate-buffered saline (PBS) or balanced salt solution (BSS), to a sterile, single-use dose of about 2-10, 2-20, 20-30, or 2-50 μg/0.1 mL, e.g., about 5 μg/0.1 mL, about 6 μg/0.1 mL, about 7 μg/0.1 mL, about 8 μg/0.1 mL, about 9 μg/0.1 mL, about 10 μg/0.1 mL. In some embodiments, the topotecan (or topotecan HCl) is used in single doses of about 5 μg/0.1 mL to about 30 μg/0.1 mL. In some embodiments, the topotecan (or topotecan HCl) is used in single doses of about 8 μg/0.1 mL. As used herein, the term "about" means plus or minus ten percent.

In some embodiments, the topotecan is formulated for sustained release. A number of sustained release formulations of topotecan are known in the art, including but not limited to preformed liposomes containing copper sulfate and the divalent metal ionophore, lipid nanoparticles, or sustained-release hydrogels (see, e.g., Patankar et al., *Invest New Drugs,* 2013 February; 31(1): 46-58; Souza et al., *Eur J Pharm Biopharm,* 2011 September; 79(1): 189-96; and Taich et al., *Colloids Surf B Biointerfaces,* 2016 Oct. 1; 146:624-31). Alternatively or in addition, sustained release can be achieved using a sustained-release device such as intravitreal implants, e.g., as described in Palakurthi et al., Current Eye Research, 35(12): 1105-1115 (2010) or similar to the Retisert (Bausch & Lomb), Ozurdex (Allergan); or non-biodegradable implants, e.g., similar to Iluvien (Alimera) or Vitrasert (Bausch & Lomb) implants; the I-vation platform (SurModics Inc.). See also Lee et al., Pharm Res. 27(10): 2043-53 (2010); Haghjou et al., J Ophthalmic Vis Res. 6(4):317-329 (2011); Kim et al., Invest. Ophthalmol. Vis. Sci. 45(8):2722-2731 (2004); and Velez and Whitcup, Br J Ophthalmol 83:1225-1229 (1999). In some embodiments, the topotecan is administered in an implant, e.g., a sustained-release implant that delivers topotecan directly to the eye over a period of up to six months. An exemplary implant made from a biodegradable polymer and placed in the vitreous humor by injection can be obtained from Ivantis. See also U.S. Pat. Nos. 9,668,915, 9,173,775, 10,285,853, US20180369017, and US20210030590.

In some embodiments, the formulation of topotecan (and optional additional agent) is optimized based on assessments of loading efficiency, influence of temperature on drug loading and in vitro stability of the resulting formulation.

Additional Therapeutic Agents

The methods and compositions described herein can include one or more additional therapeutic agents, e.g., one or more of melphalan, daunorubicin, lenalidomide, daclatsvir, stavudine, resveratrol, marbofloxacin, bendamustine hcl, semagacestat, Runx1 inhibitors, and methotrexate, or structural analogs thereof.

In some embodiments, the one or more additional therapeutic agent is melphalan. Melphalan, also known as L-phenylalanine mustard, phenylalanine mustard, L-PAM, or L-sarcolysin, is a phenylalanine derivative of nitrogen mustard. Melphalan is a bifunctional alkylating agent that is active against selected human neoplastic diseases. It is known chemically as 4-[bis(2-chloroethyl) amino]-L-phenylalanine. The molecular formula is $C_{13}H_{18}C_{12}N_2O_2$ and the molecular weight is 305.20. The chemical structure of melphalan is shown in Formula II:

Formula II

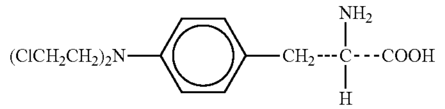

Analogues of melphalan include L-phenylalanine mustard (L-PAM or Melphalan Hydrochloride), a prodrug of melphalan that is converted to the active form of the drug in the body. It is FDA-approved for the treatment of multiple myeloma, ovarian cancer, and breast cancer. Chlorambucil is another alkylating agent that is similar in structure to melphalan. It is FDA-approved for the treatment of chronic lymphocytic leukemia, Hodgkin's disease, and non-Hodgkin's lymphoma. Cyclophosphamide is a prodrug that is converted to its active form in the liver. It is FDA-approved for the treatment of various types of cancer, including lymphomas, leukemias, and breast cancer. Busulfan is an alkylating agent that is used in the treatment of chronic myeloid leukemia, myeloproliferative disorders, and as a conditioning agent before hematopoietic stem cell transplantation. Melphalan or analogs thereof can be used as an alternative to topotecan in any of the methods or compositions described herein, including in combination with the other therapeutic agents such as RUNX1 inhibitors or daunorubicin or analogs thereof.

Analogues of daunorubicin include doxorubicin, a closely related anthracycline chemotherapy agent that has a similar mechanism of action to daunorubicin. It is FDA-approved for the treatment of various types of cancer, including breast cancer, bladder cancer, and lung cancer. Idarubicin is another anthracycline chemotherapy agent that is structurally similar to daunorubicin. It is FDA-approved for the treatment of acute myeloid leukemia. Mitoxantrone is an anthracenedione chemotherapy agent that has a similar mechanism of action to daunorubicin. It is FDA-approved for the treatment of multiple sclerosis and certain types of cancer, including breast cancer and non-Hodgkin's lymphoma.

Analogues of lenalidomide include pomalidomide, a derivative of thalidomide and a more potent immunomodulatory drug than lenalidomide. It is FDA-approved for the treatment of multiple myeloma that has relapsed or is refractory to other therapies. Thalidomide is the first-generation immunomodulatory drug that lenalidomide is derived from. It is FDA-approved for the treatment of multiple myeloma and erythema nodosum leprosum. Ixazomib is a proteasome inhibitor that, like lenalidomide, is used to treat multiple myeloma. It is FDA-approved for the treatment of newly diagnosed multiple myeloma in combination with lenalidomide and dexamethasone, and for the treatment of relapsed or refractory multiple myeloma.

RUNX1 inhibitors include Ro24-7429 and its analog Ro5-3335, as well as NSC140873, MLS000548294, MLS001048862, and NSC156594. See, e.g., Cunningham et al. (2012) Proc Natl Acad Sci USA, 109(36): 14592-14597, Haubrich, R. et al., J Infect Dis 172(5): 1246-52, and U.S. Patent Application Publication No. 2014/0004082, the entire contents of each of which are incorporated herein by reference. Additional examples of RUNX1 inhibitors are described in U.S. Pat. Nos. 5,641,773; 5,164,376; 5,141,735; 5,041,438; 5,036,101; and 3,405,122, as well as US20140004082 and US20200377888, the entire contents of each of which are hereby incorporated herein by reference.

Subjects

The methods described herein can be used to prevent (reduce the risk of) PVR or ERM in patients, e.g., in patients requiring pars plana vitrectomy (PPV), e.g., for rhegmatagenous retinal detachment secondary to trauma; for patients requiring PPV for preexisting proliferative vitreoretinopathy grade C or higher; and/or for patients with retinal detachments requiring PPV for other indications associated with high risk condition for PVR development, e.g., giant retinal tears (giant retinal tears are defined as tears involving 90° or more of the circumference of the globe), retinal breaks larger than 3 disc areas, long-standing retinal detachments, or detachments associated with hemorrhage.

In some embodiments, the subject is at least 18 years old. A person of ordinary skill in the art would understand that the doses of the active agents used in the methods described herein can be adjusted based on the age, degree of disease and other relevant conditions of the subject.

In some embodiments, the subject has failed standard of care surgery for RRD in the same eye previously. In some embodiments, the subject has previously received at least one vitreoretinal surgery for RRD, including pneumatic retinopexy, pars plana vitrectomy and/or scleral buckle, and has clinical documentation supporting redetachment of the retina after one or more vitreoretinal surgeries for RRD in the same eye. In some embodiments, the subject has an extremely guarded visual prognosis and visual potential.

In some embodiments, the subject does not have a history of tractional or exudative retinal detachment. In some embodiments, the subject does not have severe non-proliferative or proliferative diabetic retinopathy. In some embodiments, the subject does not have other planned ocular surgery following PPV. In some embodiments, the subject does not have primary RRD. In some embodiments, the subject does not have pre-existing bone marrow suppression or cytopenias. In some embodiments, the subject does not have pre-existing interstitial lung disease (ILD).

In some embodiments, in the methods described herein, the subject does not have cancer, e.g., does not have an ocular cancer, e.g., does not have intraocular retinoblastoma. In some embodiments, the methods include determining that a subject has or is at risk of developing PVR, or is about to undergo a procedure with a high risk of PVR as a side effect, and selecting the subject.

Other uses of sustained topotecan in the eye in addition to PVR include the following:

Reducing Risk of Epiretinal Membranes after Retinal Detachment (RD) Surgery

Approximately 20-30% of RD cases develop clinically perceptible ERMs. Half of these are so visually distorting that patients will require surgery. In addition, autopsy studies show that close to 75-80% of patients with RD surgery have some degree of proliferative of membranes. This may explain why many patients do not achieve perfect vision postoperatively after RD surgery, yet do not have any ERMs grossly perceptible to the human eye.

Reducing Risk of ERMs that Develop Spontaneously

ERMs can develop spontaneously, which then requires surgery. If a subject developed an ERM in one eye, implanting a device to prevent ERMs in the other eye could prevent development in that eye.

Reducing Risk of Secondary ERM after ERM Surgery

For patients who develop ERMs, these can be removed but some reoccur and require reoperation. Leaving an implant could prevent the recurrent ERM.

The methods described herein can include identifying and/or selecting a subject who is in need of treatment to prevent the development of PVR or ERM as a result of a condition listed above (e.g., selecting the subject on the basis of the need of treatment as a result of a condition listed above, e.g., an increased risk of developing PVR or ERM as a result of a condition listed above). In some embodiments, the subjects treated with a method described herein do not have ocular cancers, e.g., do not have retinoblastoma.

The presentation of PVR clinically encompasses a wide phenotype. PVR can vary from a mild cellular haze (Grade A) to thick, fibrous membranes that cause the characteristic stiffened funnel of the detached retina (Grade D). A number of grading systems are in use, see, e.g., Ryan, *Retina,* $5^{th}$ ed (Elsevier 2013); Retina Society Terminology Committee. The classification of retinal detachment with proliferative vitreoretinopathy. Ophthalmology 1983; 90:121-5 (1983); Machemer R, Aaberg T M, Freeman H M, et al. Am J Ophthalmol 112:159-65 (1991); Lean J, Irvine A, Stern W, et al. Classification of proliferative vitreoretinopathy used in the silicone study. The Silicone study group. Ophthalmology 1989; 96:765-771. In some embodiments the methods include identifying, selecting, and/or treating a subject who has a low grade (e.g., Grade A or Grade 1) PVR, or who has ERM. In some embodiments, the methods include monitoring the subject for early signs of the development of PVR or ERM, i.e., the presence of a "vitreous haze" indicating a cellular proliferation (which may eventually develop into an organized sheet), and administering one or more doses of topotecan as described herein. Although early Grade A PVR vs. an early ERM may be difficult to distinguish from one another, eventually untreated PVR will progress; ERMs will cause a mild traction on the macula resulting in metamorphopsia but will not cause detachment of the retina, whereas untreated PVR will cause detachment and eventually result in a funneled, atrophic retina. The methods can also be used to treat subjects without present signs of PVR but who are at risk for PVR or ERMs.

Methods of Treating or Reducing Risk of PVR or ERM

The methods described herein include the administration of topotecan (and/or one or more additional therapeutic agents, e.g., melphalan, daunorubicin, lenalidomide, daclatsvir, stavudine, resveratrol, marbofloxacin, bendamustine HCl, semagacestat, or methotrexate) in subjects who are at risk of developing a first or recurring PVR or ERM, e.g., a subject who is undergoing RD surgery or ERM surgery, as described above, and in subjects who have PVR or ERM or who are at risk for developing PVR or ERMs. In some embodiments, the methods described herein include the use of topotecan (and/or one or more additional therapeutic agents) in subjects who have undergone, are undergoing, or will undergo a pars plana vitrectomy (PPV) or scleral buckle (SB). In some embodiments, the methods include performing a PPV, RD surgery, or ERM surgery. Methods for performing these surgeries are known in the art; for example, typically, PPV is performed under local or general anesthesia using three, 23 or 20 gauge sclerotomy ports. Any present epiretinal membranes can be dissected, e.g., using a membrane pick and forceps. Intraoperative tissue staining, perfluorocarbons, cryopexy, endolaser, scleral buckling, and lensectomy can also be performed as needed. Standard tamponading agents can be used, e.g., silicone oil or gas.

The methods described herein include the use of an effective amount of topotecan and/or one or more additional therapeutic agents. An "effective amount" is an amount sufficient to effect beneficial or desired results, e.g., the desired therapeutic effect (i.e., a prophylactically effective amount that reduces the risk of developing PVR or ERM). An effective amount can be administered in one or more administrations, applications or dosages. A therapeutically effective amount of topotecan can be, e.g., about 5 μg/0.1 mL to about 30 μg/0.1 mL (e.g., 8 μg/0.1 mL) per injection with one or more injections. In some embodiments, the topotecan is used in one or more single doses of about 5 μg/0.1 mL, about 6 μg/0.1 mL, about 7 μg/0.1 mL, about 8 μg/0.1 mL, about 9 μg/0.1 mL, about 10 μg/0.1 mL or more. In some embodiments, the topotecan (or topotecan HCl) is used in single doses of about 5 μg/0.1 mL to about 30 μg/0.1 mL. In some embodiments, the topotecan (or topotecan HCl) is used in single doses of about 8 μg/0.1 mL. Other volumes can also be used.

In some embodiments, the methods include giving about 1, about 2, about 3, about 4, about 5, about 6, about 7, about 8, about 9, about 10 or more injections. For example, in some embodiments, the methods include giving about 7 injections of 8 μg/0.1 mL topotecan, for a cumulative dose of 56 μg. The compositions can be administered from one or more times per day to one or more times per week to one or more times per month; including once every other day or once every two, three, or four weeks. The skilled artisan will appreciate that certain factors may influence the dosage and timing required to effectively treat a subject, including but not limited to the severity of the disease or disorder, previous treatments, the general health and/or age of the subject, and other diseases present.

In some embodiments, intravitreal topotecan injections are performed aseptically after the topical application of anaesthesia and an antiseptic agent, e.g., 5% povidone iodine, to the conjunctival sac. In some embodiments, each subject receives an intravitreal injection of topotecan, e.g., 8 μg/0.1 mL topotecan, 3.0 to 3.5 mm posterior to the limbus, depending on lens status, with a 30-gauge needle.

In some embodiments, the topotecan is administered preoperatively, intraoperatively during surgery, and/or postoperatively. In some embodiments, the surgery comprises pars plana vitrectomy with or without scleral buckle.

In some embodiments, the topotecan is administered preoperatively for about 1, 2, 3, 4, 5 or more times. In some embodiments, the topotecan is administered preoperatively about 1, about 2, about 3, about 4 or more weeks before the surgery. In some embodiments, the topotecan is administered preoperatively within one week from surgery. In some embodiments, the topotecan is administered preoperatively once within one week from surgery.

In some embodiments, the topotecan is administered intraoperatively during surgery for about 1, 2, 3, 4, 5 or more times. In some embodiments, the topotecan is administered intraoperatively during surgery once.

In some embodiments, the subjects receive multiple intravitreal injections of topotecan postoperatively (during their post-operative period). Injections can be administered on post-operative (post-op) weeks 1, 2, 3, 4, 5, 6, 7, 8, 10, 12, and 14, and on post-op month 4, for a total of about 1, 2, 3, 4, 5, 6, 7, 8, 9, 10 or more injections. In some embodiments, the methods include administering the topotecan in seven doses, or seven or more doses, or less than seven doses, over a four-month period or longer, and injections would be given no more frequently than weekly (e.g., biweekly). In some embodiments, the methods include additional doses at weekly, biweekly, or monthly frequency thereafter for an additional one, two, three, four, five, six, seven, eight, nine, ten, 11, or 12 months thereafter.

In some embodiments, a first injection is given preoperatively within one week from surgery; a second injection is given intraoperatively during surgery; and five injections are given postoperatively every two weeks, with an optional additional one or more doses at monthly intervals thereafter for an additional one, three, six, or more months thereafter. In some embodiments, intravitreal topotecan 8 μg/0.1 mL, administered preoperatively within one week from surgery, intraoperatively during surgery, as well as postoperatively at 2 weeks, 4 weeks, 8 weeks, 12 weeks and 16 weeks, for a total of 7 injections.

In some embodiments, the subjects receive a sustained release implant, e.g., as described above, that will release topotecan over time, e.g., over a week, two weeks, a month, two months, three months, six months, or a year. In some embodiments, the methods include administering subsequent implants to provide topotecan administration for at least six months, one year, two years, or more.

In some embodiments, the topotecan is administered as the sole active agent. In some embodiments, the topotecan is administered in combination with one or more additional therapeutic agents, e.g., as described herein, either in a single composition or in two or more combinations. Also provided herein are the compositions comprising topotecan as the sole active agent or in combination with other additional therapeutic agents as described herein, e.g., for use in a method described herein. In some embodiments, the additional therapeutic agent is administered simultaneously with the topotecan, e.g., in the same composition or at the same time.

EXAMPLES

The invention is further described in the following examples, which do not limit the scope of the invention described in the claims.

Example 1. Efficacy of Intravitreal Topotecan on Patient-Derived Model of Proliferative Vitreoretinopathy In this study, the anti-inflammatory, anti-proliferative and anti-fibrotic activities of intravitreal topotecan were tested using a patient-derived model of proliferative vitreoretinopathy. The efficacy for intravitreal topotecan was tested in cell cultures of PVR.

Twelve candidate drugs were tested at 2 concentrations at 72 hours for their effects on proliferation and cytotoxicity in C-PVR cells. The most significant hits were tested in combination with other compounds to study combinatorial effects on proliferation. This effect was further evaluated in an ex vivo explant model, and total branch lengths were measured. Human patient derived primary cultures of PVR (C-PVR cells) were cultured and seeded into 96 well assay plates and the effect of anti-proliferative drugs: melphalan and topotecan HCl was evaluated. Each anti-proliferative drug was tested at 2 concentrations determined by using the IC50 of each drug. The data was expressed as percent cell inhibition.

Figure 1B:
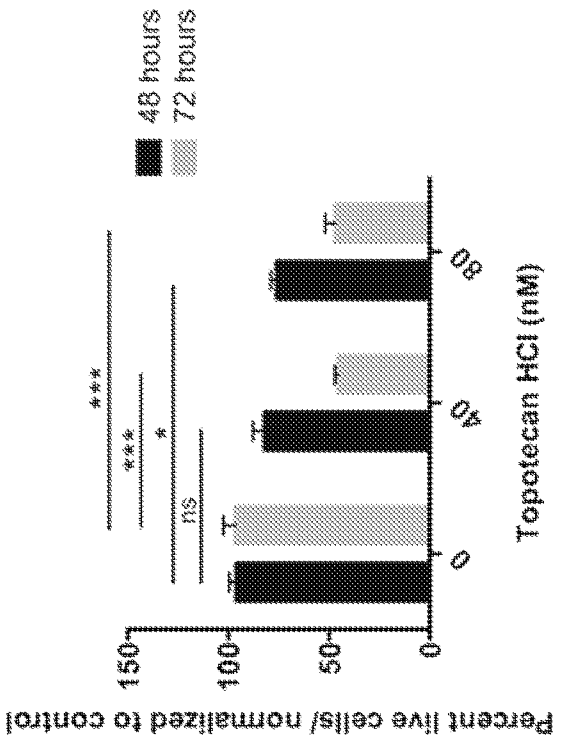
Figures 2A, 2B:
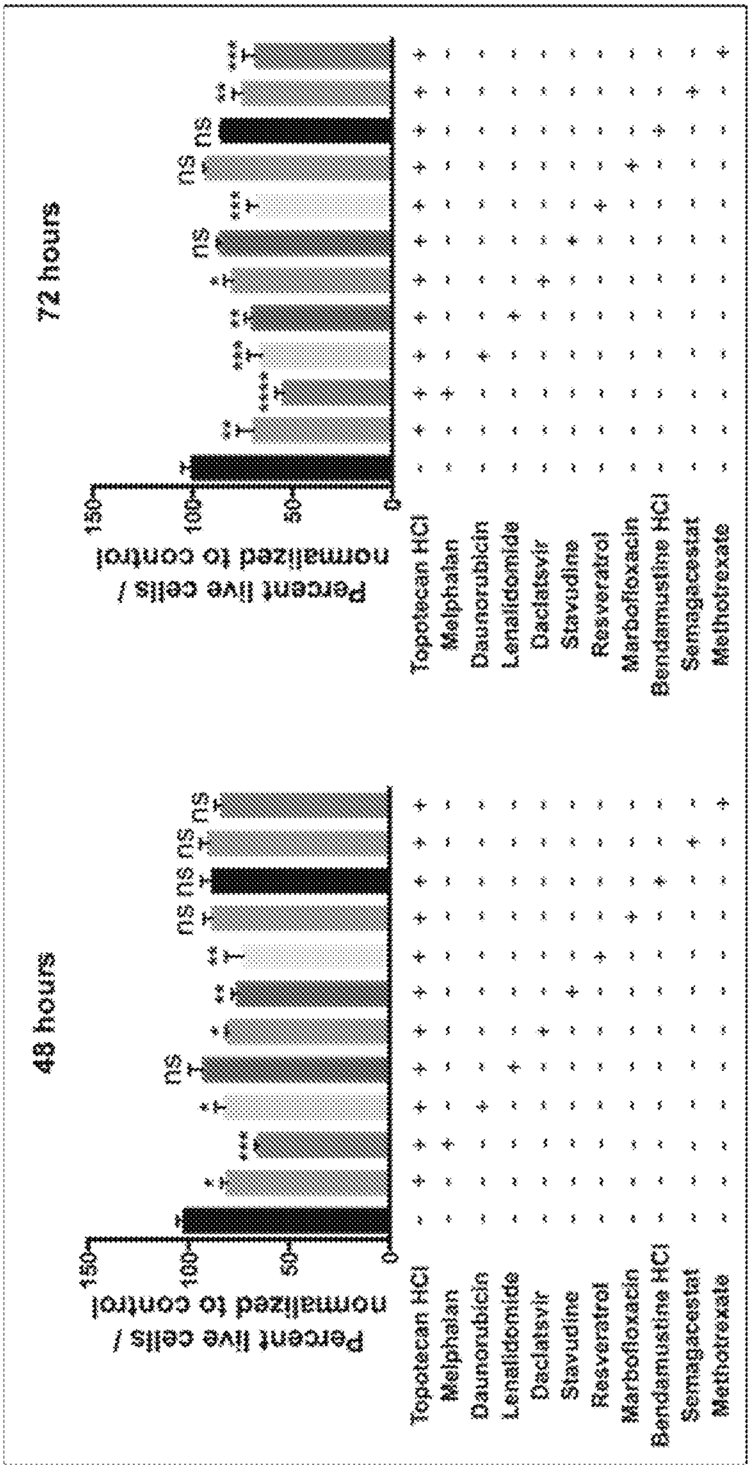
FIGS. 2A-2B show the effect of drug combination on the proliferation of human patient derived primary cultures (C-PVR).
Figures 3A, 3B:
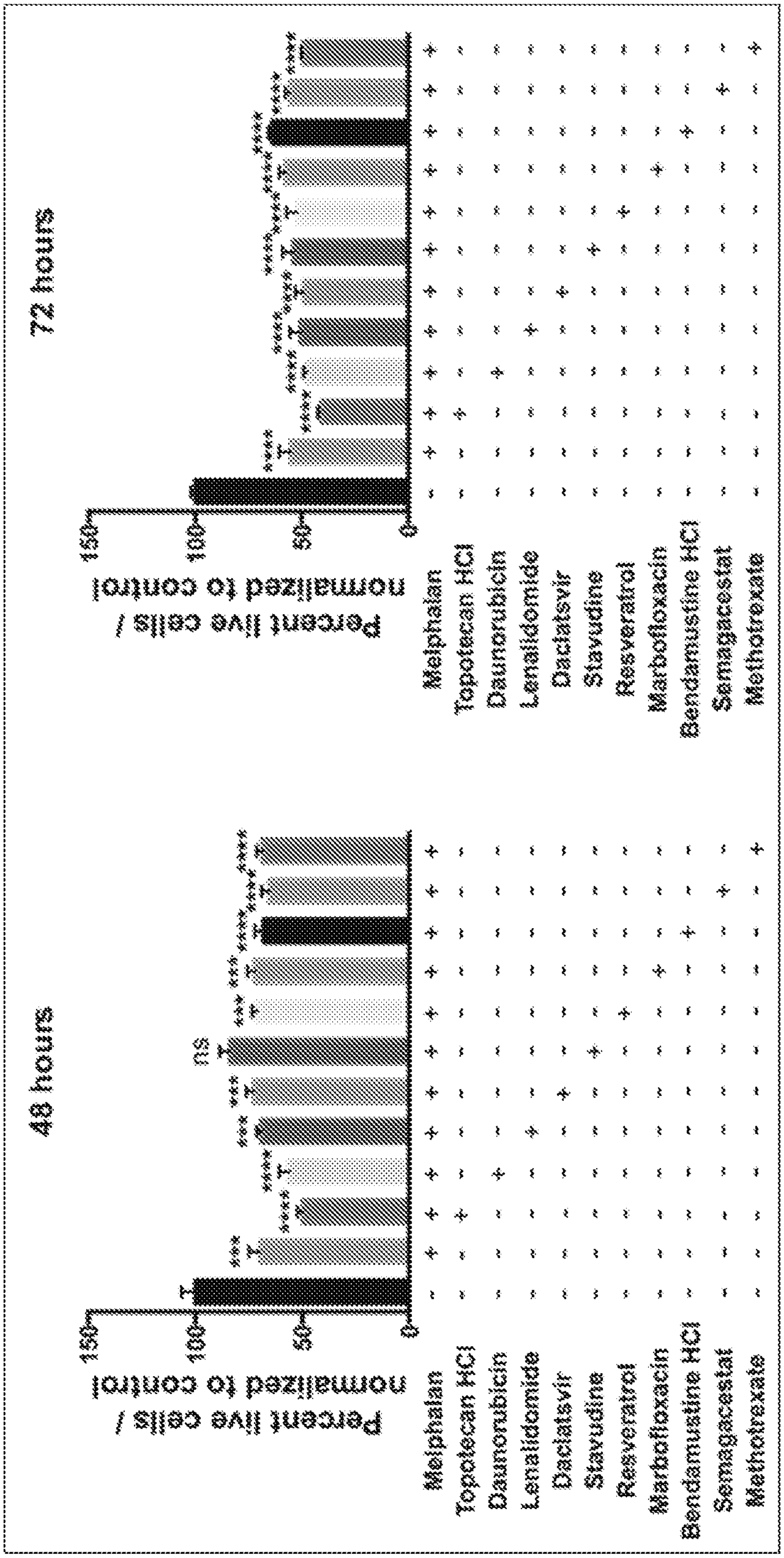
FIGS. 3A-3B show the effect of drug combination on the proliferation of human patient derived primary cultures (C-PVR).

As shown in FIG. 1A, melphalan effectively inhibited the proliferation of C-PVR cells at concentrations of 30 nM and 60 nM. As shown in FIG. 1B, topotecan HCl effectively inhibited the proliferation of C-PVR cells at concentrations of 40 nM and 80 nM. The inhibition of proliferation by melphalan or topotecan HCl was in a dose-dependent and time-dependent manner.

As shown in FIGS. 2A-2B and FIGS. 3A-3B, topotecan HCl in combination with other candidate drugs showed significant inhibition of proliferation of C-PVR cells. At 5 μM concentration 6 out of 12 drugs, bendamustine, semagacestat, daclatsvir, marbofloxacin, stavudine, and resveratrol significantly inhibited cell proliferation (20%, 30%, 16%, 30%, 19%, and 28% inhibition respectively). At 1 μM concentration, 2 out of 12 drugs, bendamustine (25%) and semagacestat (28%) significantly inhibited proliferation. 30 μM melphalan induced 74% inhibition, and a 60 μM concentration reduced cell proliferation by 83%. Topotecan at 40 nM induced a 54% decrease in proliferation, and a 53% decrease was noted with 80 nM. Daunorubicin, 15 nM treatment resulted in a 50% reduction, while the 30 nM treatment resulted in a 53% reduction in proliferation. Likewise, with lenalidomide, 24% inhibition of proliferation was observed. The combination of melphalan or topotecan with other drugs showed a dramatic effect on the proliferation of C-PVR cells. Melphalan showed synergistic effect with all 10 drugs. In comparison, when treated with topotecan 6 out of 10 showed a synergistic effect in combination. No significant cell death was observed.

To test the effect of the anti-proliferation drugs on cell outgrowths and sprouting in human PVR explants, PVR membrane fragments after surgery were placed on a Matrigel mount with C-PVR cell growth media and treated with melphalan (30 μM), topotecan HCl (80 nM), alone or in combination and control explant with no drug. This effect of combination therapy were further evaluated in the ex vivo explant model, and total branch lengths were measured.

Figure 4A:
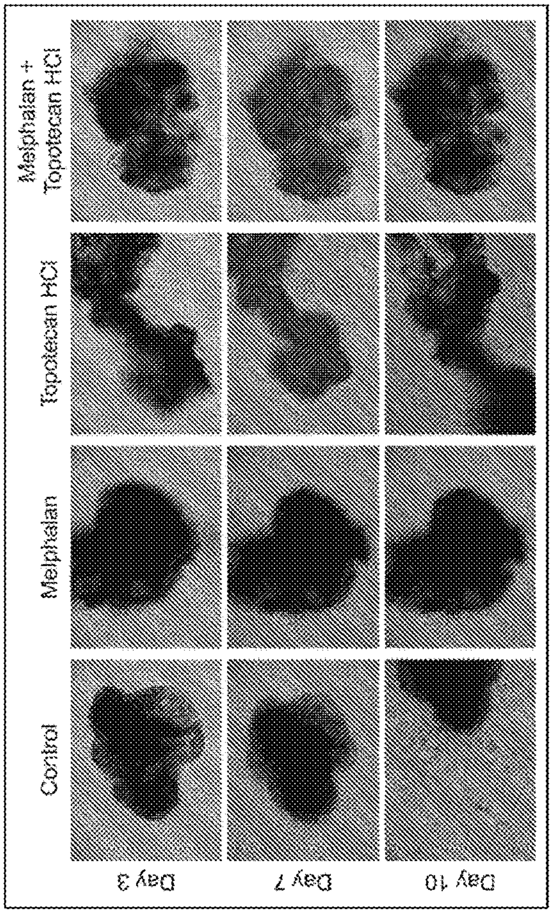
FIGS. 4A-4B show the cell outgrowths and sprouting in human PVR explants treated with topotecan and/or melphalan. Fewer outgrowths and a statistically significant reduction in sprouting distance from the explant was observed 3-10 days in explant treated with melphalan alone (30 μM), topotecan alone (80 nM) or a combination treatment with melphalan and topotecan.
Figure 4B:
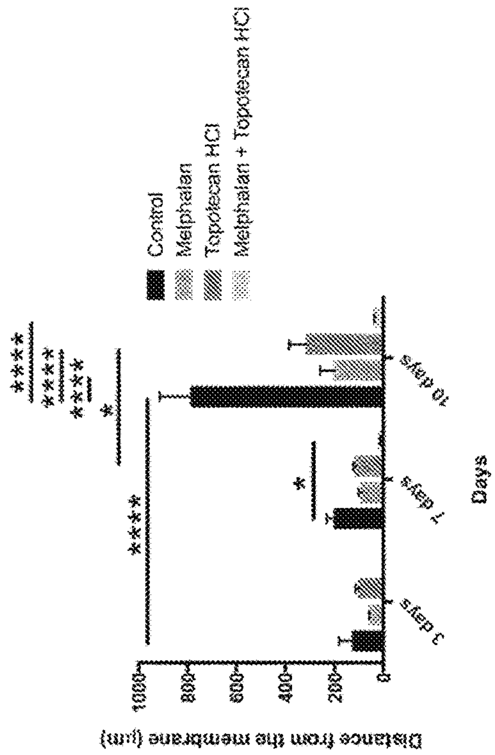

As shown in FIGS. 4A-4B, melphalan and topotecan HCl inhibited outgrowths in an ex-vivo model of PVR. Melphalan at 30 μM (27.5 mm total branch length) and topotecan at 40 nM (34 mm total branch length) alone reduced the distance covered by outgrowths compared to vehicle (167 mm total branch length) in the explants. Explants treated with combination therapy showed an almost complete inhibition of any growth suggesting synergistic effect.

The expression of the presumed target of topotecan, Topoisomerase 1 (TOP1) was also examined in patient-derived scRNA-seq. Specifically, PVR specimens were collected from patients in the operating room during surgery for retinal detachment. Samples were transported in saline and submitted for single-cell RNA sequencing using a 10× Chromium library prep. Due to the limited number of cells in each sample, single-cell RNA sequencing counts were combined across seven patient-derived proliferative vitreoretinopathy membranes (5 epiretinal membranes, 1 ciliary body membrane and 1 subretinal membrane). The total number of cells was 5,087. Expression vectors underwent standard normalization procedures using a log transform.

Figure 5A:
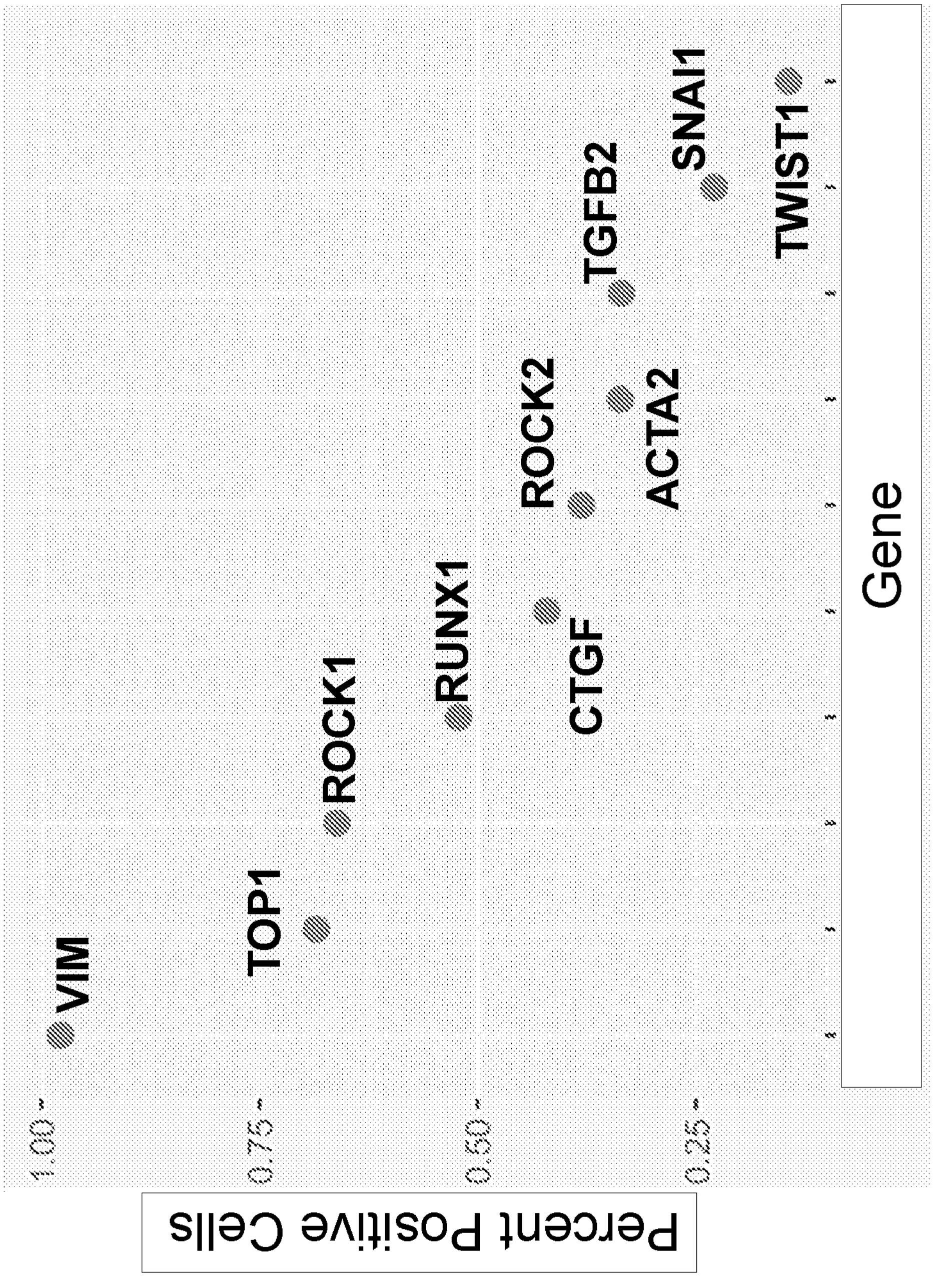
FIGS. 5A-5B show the expression of Topoisomerase 1 (TOP1, the target of topotecan) in patient-derived PVR membranes. Though the absolute expression of TOP1 is lower than VIM and ACT2A, it was almost universally expressed in the cells suggesting importance.
Figure 5B:
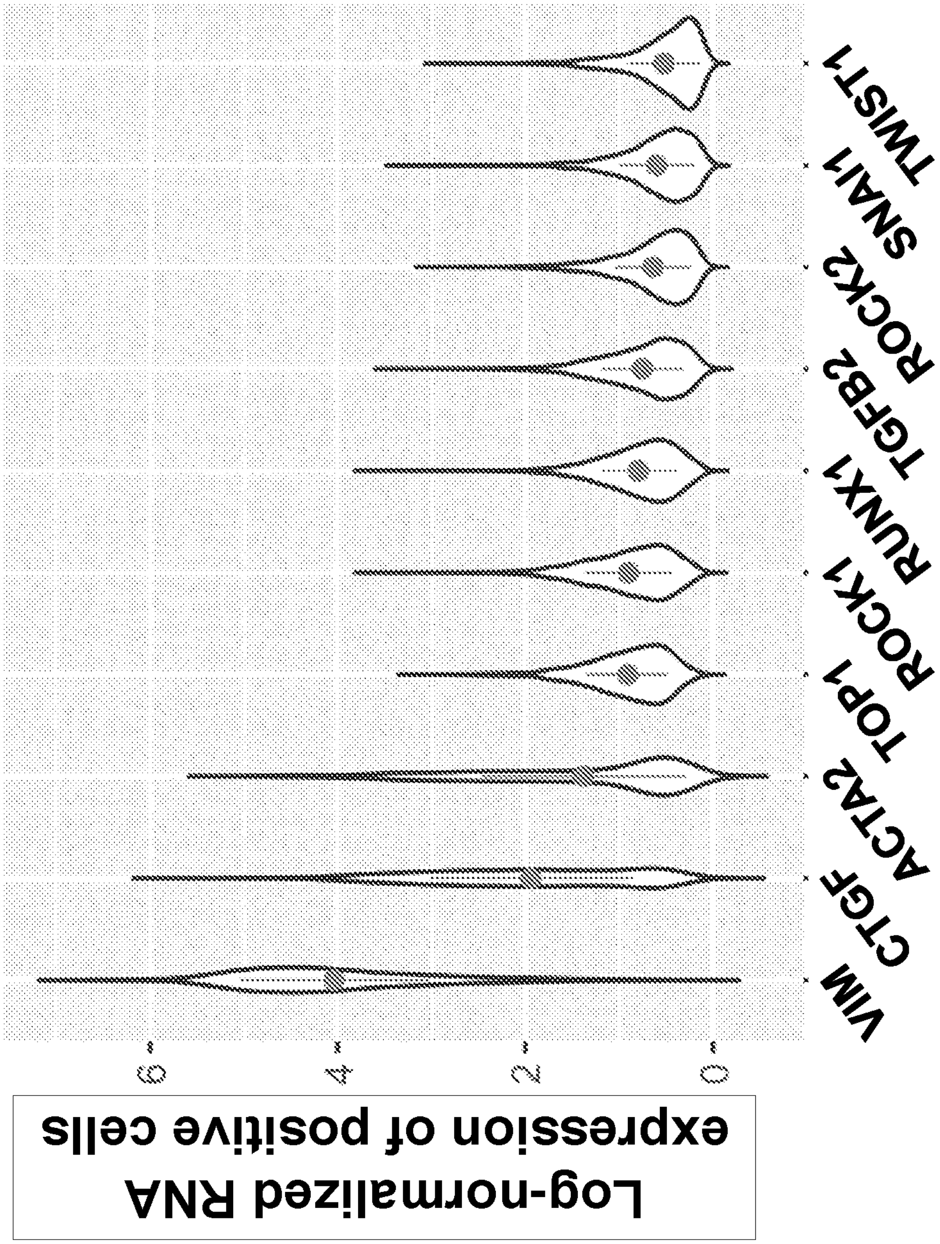

As shown in FIGS. 5A-5B, robust Topoisomerase 1 expression and robust RNA expression was detected in a majority of cells within PVR membranes, suggesting that TOP1 can be effectively targeted by the treatment with topotecan.

These results show that melphalan and topotecan HCl showed dose and time dependent effects on C-PVR cell proliferation. Melphalan has significant dose-dependent effects on C-PVR. Melphalan and topotecan in combination with other drugs successfully inhibited the proliferation and growth of PVR in vitro, and results showing almost complete inhibition of any growth in an explant model of PVR demonstrated synergistic effects of these agents when used as combination therapy.

To evaluate the effects of combination therapy with RUNX1 inhibitors, CPVR cells were cultured in 96 well plates for 8 hours, followed by treatment with RUNX1 inhibitor (Ro5-3335, Calbiochem), or Melphalan (Selleckchem), or Topotecan HCl (Selleckchem), or Daunorubicin HCl in growth media or vehicle only for a period of 48 or 72 hours. The cells were washed and the CyQuant Direct nucleic acid stain was added and incubated at 37 degrees in the incubator. Fluorescence read outs were measured at wavelengths as instructed in the protocol.

Figure 6A:
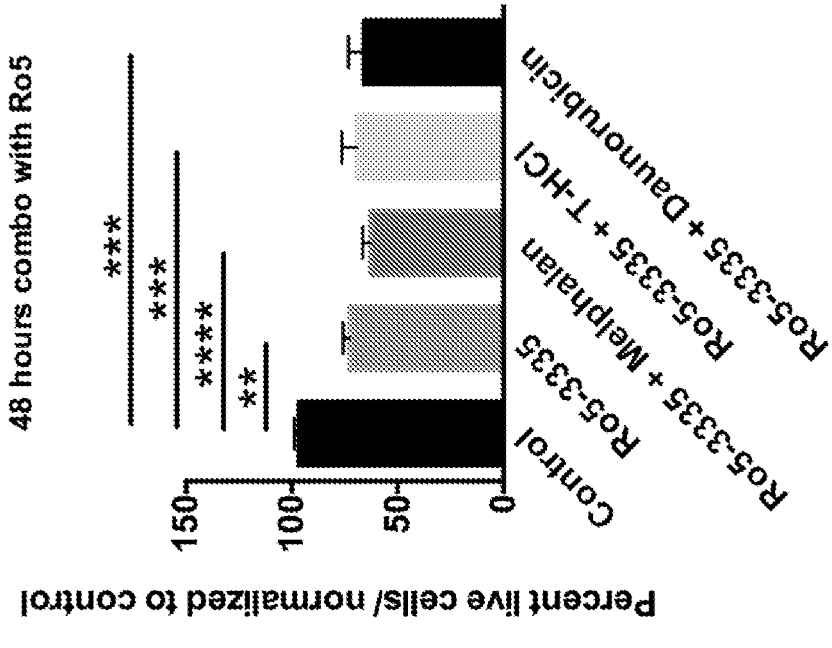
FIGS. 6A-B show that Runx1 inhibition was efficacious at inhibiting growth of C-PVR cells but in combination with Melphalan, or Topotecan HCl or Daunorubicin HCl it showed an almost complete inhibition of proliferation of the C-PVR cells. CyQuant Cell Proliferation Assay 48 (FIG. 6A) and 72 hours (FIG. 6B) post treatment with RUNX1 inhibitor 150 μM, alone or in combination with Melphalan 30 μM, or Topotecan HCl or Daunorubicin HCl compared to vehicle treated showed a significant reduction in percent live cells at 48 hours and an even greater or almost complete inhibition at 72 hours. *P<0.05, P<0.01, *P<0.001, ****P<0.0001.
Figure 6B:
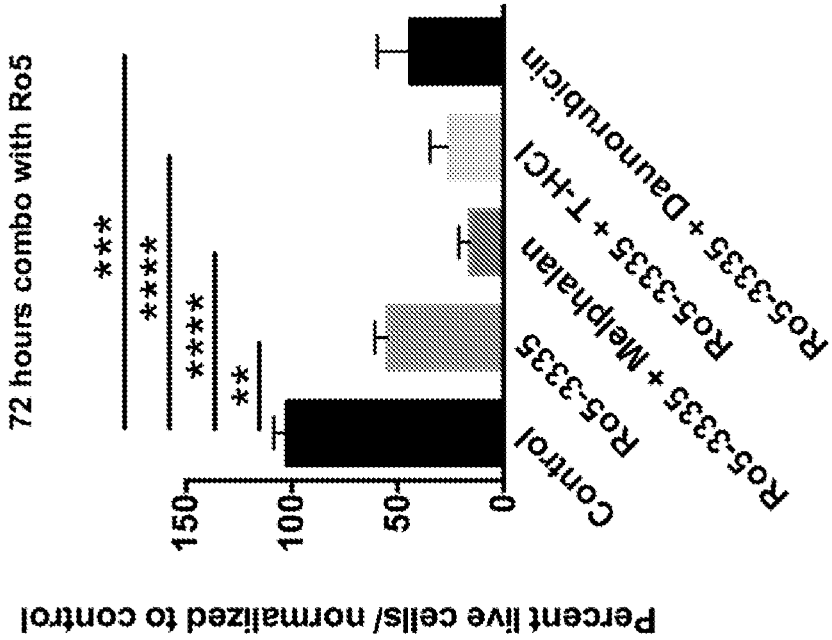

The results, shown in FIGS. 6A-6B, showed that Runx1 inhibition was efficacious at inhibiting growth of C-PVR cells but in combination with Melphalan, or Topotecan HCl or Daunorubicin HCl it showed an almost complete inhibition of proliferation of the C-PVR cells. It also showed that Runx1 inhibition can be used as an adjuvant in combination to treatments like melphalan, or Topotecan HCl or Daunorubicin HCl and that the effect could be additive or synergistic.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating proliferative vitreoretinopathy (PVR) in a subject, the method comprising administering to the subject multiple intravitreal injections of topotecan over a period of at least one, two, three, four, or more months, given no more frequently than weekly.

2. The method of claim 1, comprising administering five or more intravitreal injections of topotecan.

3. The method of claim 2, comprising administering seven intravitreal injections of topotecan.

4. The method of claim 1, wherein each injection provides a dose of about 5 mcg, about 6 mcg, about 7 mcg, about 8 mcg, about 9 mcg, or about 10 mcg topotecan, preferably administered in a volume of 0.1 ml.

5. The method of claim 4, wherein each injection provides a dose of about 8 mcg topotecan, preferably administered in a volume of 0.1 ml.

6. The method of claim 1, wherein the subject is undergoing an ocular surgical procedure that increases the subject's risk of developing PVR.

7. The method of claim 6, wherein the ocular surgical procedure is a pars plana vitrectomy (PPV), Retinal Detachment (RD) surgery; ERM surgery; scleral buckle surgery; or a procedure in the other eye.

8. The method of claim 6, wherein the subject requires a PPV to treat a rhegmatagenous retinal detachment (RRD) secondary to trauma; preexisting proliferative vitreoretinopathy; or for other indications associated with high risk condition for PVR development.

9. The method of claim 8, wherein the indication associated with high risk condition for PVR development is a giant retinal tear, a retinal break larger than 3 disc areas, a long-standing retinal detachment, or a detachment associated with hemorrhage.

10. The method of claim 6, wherein the topotecan is administered preoperatively, intraoperatively during surgery, and/or postoperatively.

11. The method of claim 10, wherein:

a first injection is given preoperatively within one week from surgery;

a second injection is given intraoperatively during surgery; and five or more injections are given postoperatively, preferably at 2 weeks, 4 weeks, 8 weeks, 12 weeks and 16 weeks postoperatively.

12. The method of claim 11, comprising administering additional injections after the seventh injection.

13. The method of claim 1, wherein the topotecan is administered in combination with one or more additional therapeutic agents.

14. The method of claim 13, wherein the one or more additional therapeutic agents is selected from the group consisting of melphalan, daunorubicin, lenalidomide, daclatsvir, stavudine, resveratrol, marbofloxacin, bendamustine HCl, semagacestat, methotrexate, and a Runx1 inhibitor, or an analogue thereof.

15. The method of claim 14, wherein the one or more additional therapeutic agents is administered simultaneously with the topotecan.

16. The method of claim 1, wherein the topotecan is administered posterior to the limbus.

17. A method of treating proliferative vitreoretinopathy (PVR) in a subject, the method comprising intravitreally administering to the subject a sustained release formulation of topotecan over at least a four-month period.

18. The method of claim 17, wherein the sustained release formulation is or comprises a lipid-encapsulated formulation; multivesicular liposome (MVL) formulations of topotecan; nano- or microparticles; polyion complex (PIC) micelles; or bioadhesive polymers.

19. The method of claim 18, wherein the bioadhesive polymers comprise one or more of hydroxypropyl methylcellulose (HPMC), carboxymethylcellulose (CMC), polyacrylic acid (PAA), or hyaluronic acid (HA).

20. A method of treating proliferative vitreoretinopathy (PVR) in a subject, the method comprising implanting into the eye of the subject a device that provides sustained release of topotecan, and optionally one or more additional therapeutic agents, over at least a four-month period, preferably wherein the device is implanted within a week before the subject undergoes an ocular surgical procedure that increases the subject's risk of developing PVR.

* * * * *